United States Patent [19]

Krupnick et al.

[11] Patent Number: 4,867,146
[45] Date of Patent: Sep. 19, 1989

[54] EYE PATCH

[75] Inventors: Steven B. Krupnick, Philadelphia, Pa.; Gary F. Carlson, Cherry Hill, N.J.

[73] Assignee: Webb Research, II, Inc., Philadelphia, Pa.

[21] Appl. No.: 152,184

[22] Filed: Feb. 4, 1988

[51] Int. Cl.$^4$ .............................................. A61F 9/04
[52] U.S. Cl. ........................................... 128/858; 2/15
[58] Field of Search ................. 128/132 R, 76.5, 163, 128/156; 604/308; 2/15

[56] References Cited

U.S. PATENT DOCUMENTS

| | | | |
|---|---|---|---|
| 2,572,638 | 10/1951 | Loos | 2/15 |
| 3,068,863 | 12/1962 | Bowman | 128/132 |
| 3,092,103 | 6/1963 | Mower | 128/132 |
| 3,140,572 | 7/1964 | Petersen | 53/450 |
| 3,212,495 | 10/1965 | Osbourn et al. | 128/156 |
| 3,300,786 | 1/1967 | Rosenvold et al. | 128/132 R |
| 4,122,847 | 10/1978 | Craig | 128/132 R |
| 4,134,401 | 1/1979 | Galician | 128/157 |
| 4,450,845 | 5/1984 | Engel | 128/743 |
| 4,649,908 | 3/1987 | Ghaly | 128/132 R |
| 4,682,371 | 7/1987 | Heltman | 128/132 R |
| 4,727,869 | 3/1988 | Leonardi | 128/163 |

Primary Examiner—Edgar S. Burr
Assistant Examiner—Huong Q. Pham
Attorney, Agent, or Firm—Caesar, Rivise, Bernstein, Cohen & Pokotilow, Ltd.

[57] ABSTRACT

An eye patch is provided for preventing opening of an eye and preventing corneal abrasion. The patch comprises a compressible planar pad having a configuration which fits within the eye socket to permit easy contact with the outer surface of the eyelids over a closed eye. The planar pad is flexible to facilitate conforming to the outer surface of the lids of the eye. One surface of the pad has an adhesive with a low to moderate adhesion applied thereto to permit securement of the lids in a closed position while permitting removal of the patch with minimal patient discomfort.

8 Claims, 2 Drawing Sheets

EYE PATCH

This invention relates generally to medical bandages and more particularly to an eye patch for preventing opening of an eye.

BACKGROUND ART

During an operation while a patient is under anesthesia the muscles become relaxed and there is a tendency of the eye to open and thereby cause drying out of the eye due to exposure of air as well as drying effect caused by anesthesia. This condition is normally prevented by the use of adhesive bandages. If the eye is allowed to open, because of the dried condition of the eye and the lack of fluid between the inner surface of the eyelid and the outer surface of the eye corneal abrasion can be caused by movement of the eyelid over the eye.

In addition, after an operation on the eye or the muscles surrounding the eye, it is frequently desirable in order to speed healing and/or prevent further damage to the eye to prevent the eye from being opened. In order to accomplish the task of maintaining the eye closed by keeping the eyelids together, medical grade adhesive tape is applied over the closed eye and securing the tape to the outer surface of the eyelids to keep the eye closed. Among the disadvantages of the adhesive tape are that in order to apply any liquids to the eye for facilitating healing, the adhesive tape must be removed. Removal of the adhesive tape often causes not only pain to the eyelids of the person upon whom the tape is applied but also often causes removal of the eyelashes. Even where the tape is only removed once, the removal can be very painful. Where the removal is required often, there can be damage to the eyelids. In addition, when the eye gets too wet and the adhesive tape is loosened it can permit abrasion of the eye by coming in contact with the eye.

OBJECTS OF THE INVENTION

It is therefore an object of this invention to overcome the aforementioned disadvantages of the prior art.

A primary object of the invention is to prevent drying of the eye during an operation and thereby prevent corneal abrasion by providing a new and improved patch which overcomes the disadvantages of the prior art.

Another object of the invention is to provide a new and improved eye patch for preventing opening of an eye which utilizes a medical grade of adhesive having low to moderate adhesion to lower the pain of removal of the eye patch.

Another object of the invention is achieved by providing a compressible and flexible pad having a configuration which fits within the normal eye socket to contact the surface over a large area of the eyelids of a closed eye.

Still another object of the invention is to provide a new and improved eye patch which facilitates application of fluids to the eyes without removing the patch.

Yet another object of this invention is to provide a new and improved eye patch which includes a tab which extends laterally from the large portion of the patch covering the eye to facilitate removal and applying of the patch by enabling the tab to be easily engaged for removal or application of the patch while maintaining sterility.

These and other objects are achieved by providing an eye patch for preventing opening of an eye which comprises a compressible and flexible pad having a configuration which fits within the eye socket to enable securement to the outer surface of the eyelids of a closed eye. The pad is normally planar and conforms to the outer surface of the lids of the eye. One surface of the pad has a medical grade adhesive with a low to moderate adhesion applied thereto to permit securement of the patch to the lids in a closed position while permitting removal of the patch with a minimum of pulling on eyelashes.

The patch may also include openings to permit application of fluids to the eyes without removing the patch from the outer surface of the lid. In addition, a tab is provided which extends laterally from the portion of the patch covering the eyelid.

BRIEF DESCRIPTION OF THE DRAWINGS

Other objects and many of the attendant advantages of this invention will be readily appreciated as the same becomes better understood by reference to the following detailed description when considered in connection with the accompanying drawings wherein.

DESCRIPTION OF THE PREFERRED EMBODIMENT OF THE INVENTION

Figure 1:
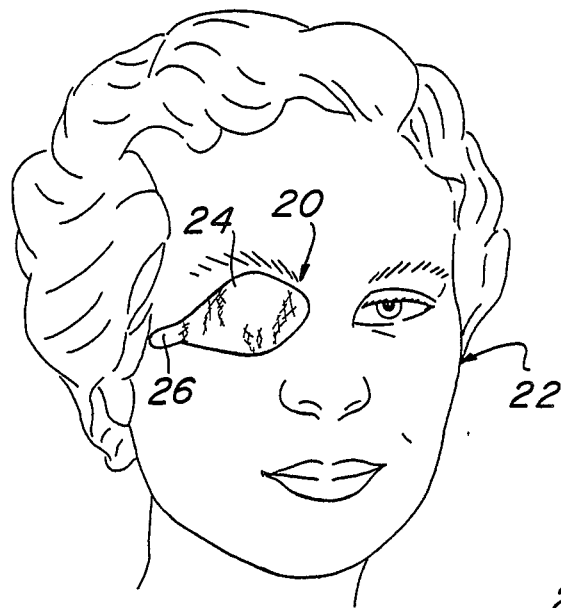
FIG. 1 is a front elevational view of a patient wearing an eye patch embodying the invention.

Referring now in greater detail to the various figures of the drawings wherein like reference characters refer to like parts, an eye patch embodying the invention is shown generally at 20 in FIG. 1.

The eye patch 20 is applied to the eye of a patient 22 as shown in FIG. 1. The patch includes a pad 24 having a laterally extending integral tab 26.

Figure 2:
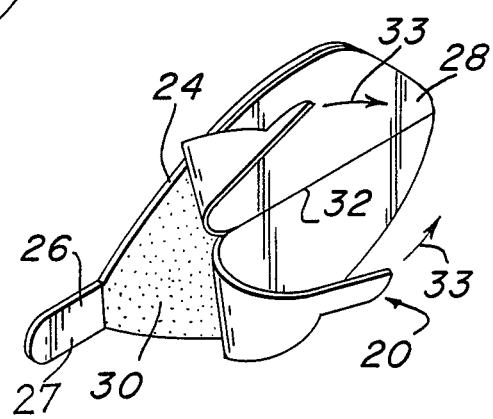
FIG. 2 is an enlarged perspective view prior to the application of the eye patch to the patient.

As best seen in FIG. 2 where the patch is shown, prior to application of the patch to the patient, an adhesive liner 28 is provided which is secured to the pad 24 by an adhesive 30 which is provided on the inner surface of the patch on the pad portion 24.

The pad 24 is preferably comprised of a medical grade polyurethane or polyethylene foam as well as any other suitable foam such as polyethylene. The tab 26 is made from the same sheet of foam. The foam may comprise an open cell or closed cell foam. The thickness of the foam is preferably 1/16" and the pad is normally planar. The outline of the pad 24 is configured to fit within the eye socket of a patient. The pad 24 is preferably flexible so that it may conform to the outer surface of the eyelids when closed.

While laterally extending tab 26 is integrally connected to the pad 24 and is made from the same sheet of foam, the inner surface of the tab 26 contains a coating of adhesive 30 which is covered by a thin sheet of paper 27 which is applied prior to the cutting of the patch.

Liner 28 is preferably comprised of a plastic sheet or smooth surfaced sheet lining material which facilitates the removal of the liner 28 from the adhesive 30 to remove the liner from the pad 24. The liner 28 is preferably one piece and may also include a slit 32 which separates the liner 28 into two pieces for ease of removal.

The liner 28 has the same outline as the pad and tab 24 and 26, respectively, so that it fits over and is aligned with both the pad and tab to keep the inner surface thereof sterile.

The adhesive 30 is preferably a medical grade adhesive with a low to moderate adhesion which is strong enough to removably secure the pad to the eyelids to prevent the eyelids from opening once the pad 24 has been applied against the outer surface of the eyelids yet of a low enough adhesion to permit the removal of the patch from the eye without causing considerable pain to the eyelids of the patient and minimizing removal of eyelashes.

In use, the pad 24 has liner 28 removed by engaging the portion of liner 28 which is adjacent the tab 26. Because of the fact that the adhesive is blocked on the inner surface of the tab, the liner 28 is separated easily from the tab 26 and the liner is removed by pulling the tab portion of the liner 28 in the direction of arrows 33 thereby peeling away the lining from the pad.

It should also be noted that closed cell foam is used for the eyepatch in applications where fluids should not reach the eye. The shape and flexibility of the pad, because it conforms to the outer surface of the eyelids, further facilitates the providing of a moisture barrier.

Figure 3:
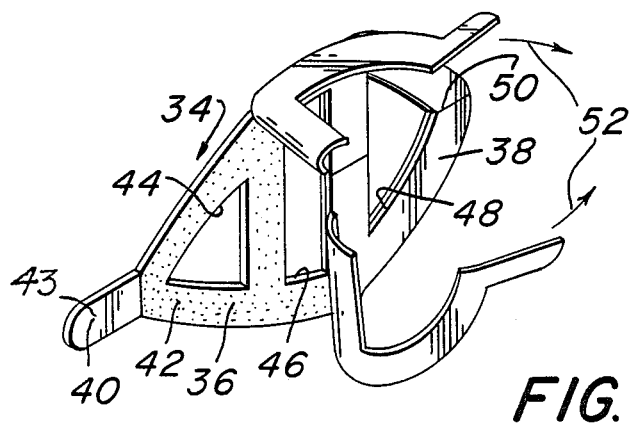
FIG. 3 is a view similar to FIG. 2 of an alternate embodiment of the invention.

The alternate embodiment of the patch embodying the invention is shown in FIG. 3 and comprises a pad 36 a liner 38 and a tab 40. The patch 34 has applied thereto on the inner surface a coating of an adhesive 42 which is like adhesive 30. The coating of adhesive 42 is blocked on tab 40 by a thin sheet of paper 43 which is formed like sheet 27 of the preferred embodiment.

In addition to the similar components of the preferred embodiment, the patch 34 further includes openings 44, 46 and 48 in the patch 34 which are provided to enable fluid to be easily applied to the eyelid while the eye patch is secured to the outer surface of the eyelids to prevent the eye from being opened inadvertently while the eye patch 34 is secured to the eye.

The liner 38 is shown having a slit 50 through the center thereof to facilitate removal in two pieces as shown by arrows 52. However, it should be noted that the removal of the liner is also facilitated by the tab 40 having the adhesive on the inner surface therof blocked by paper 43, thereby permitting easy removal of the liner.

The slit 50 which like slit 32 of patch 20 is optionally provided further facilitates removal of the liner to permit application of the eye patch to the eye.

It should be noted that openings 44, 46 and 48 cause the formation of a pair of strips between the openings that extend transversely across the border between the eyelids. The strips are each adhesively secured to the top and bottom lids and over the eyelashes to enable a suitable securement of said lids to prevent opening of the eye.

Figure 4:
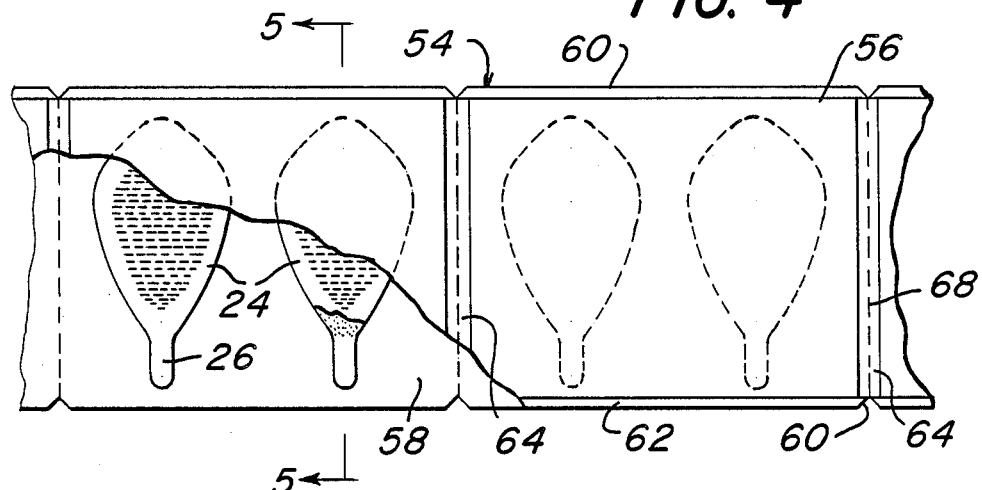
FIG. 4 is a top plan view of strip packaging for a plurality of patches embodying the invention with portions removed for purposes of clarity.
Figure 5:
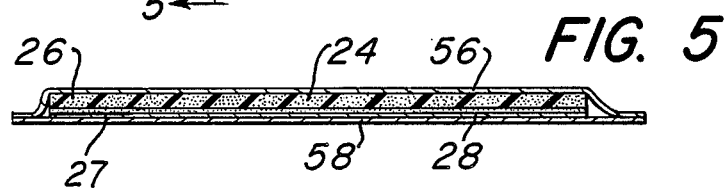
FIG. 5 is an enlarged sectional view taken along the lines 5—5 in FIG. 4.

A preferred embodiment of the packaging of the invention is shown in FIG. 4. The packaging 54 basically comprises a top and bottom sheet 56 and 58 which are elongated in a strip form. Both the top and bottom sheet 56 and 58, respectively, are preferably comprised of a plastic or coated paper and are sealed together along longitudinal edges 60 and 62 preferably by heat sealing. In addition, the top and bottom sheet of the cover are secured to each other along transversely extending edges 64 with the space between sealed transverse edges 64 being wide enough to permit two patches 24 to be provided therebetween.

Each of the transversely extending edges 64 which are heat sealed include at each end an index notch 60 and a plurality of openings or slits 68 which extend along the length of the strip 64.

The notches are provided for machine indexing and to facilitate tearing off one package which is formed between two sequentially formed edges 64. The perforation 68 further facilitates easy separation of a package of two from the strip of packaged patches.

Figure 6:
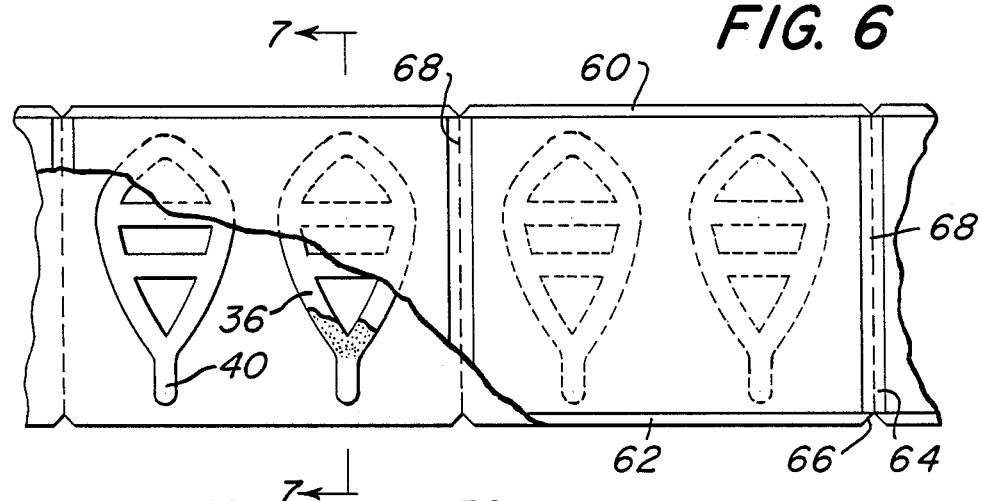
FIG. 6 is a top plan view of strip packaging for a plurality of the alternate patch embodying the invention with portions removed for purposes of clarity.
Figure 7:
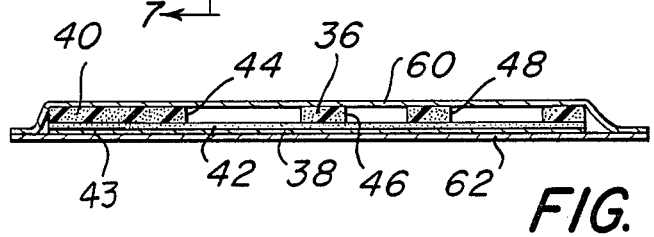
FIG. 7 is an enlarged sectional view taken along the lines 7—7 in FIG. 6.

As can be seen in FIG. 6 and FIG. 7, the packaging for the alternate embodiment of the eye patch is identical.

In addition to providing large openings such as the opening shown in connection with the alternate embodiment of the patch 34 at 44, 46 and 48, a suitable pattern of small perforations may also be provided in the foam pad portion of the patch. Such a pattern of openings is shown on the pads 24 and illustrated in FIG. 4. Where an open cell foam is used, perforations may or may not be required.

It can therefore be seen that a new and improved eye patch for preventing opening of an eye is provided. This patch protects the eye during use of anesthesia from opening in a relaxed state and thereby preventing corneal abrasion. The patch preferably includes a compressible planar pad which facilitates application to the eye by being conformable to the eye and of a shape which fits easily within the eye socket of the patient.

In addition, the cushioning of the pad further protects the eye against harm to the repaired tissue when the patch is applied to the eye as well as after the patch has been secured to the eye.

The tab on the patch not only facilitates removal of the patch after it has been secured to a patient's eyelids but also facilitates removal of the liner by having the adhesive on the inner surface thereof blocked by the paper cover.

The provision of openings further facilitates application of fluids or medication to the eye without requiring removal of the patch.

In addition, a unique strip packaging is provided which is heat sealed along the edges to provide a sterile sealed package for each pair of patches which may be easily opened and easily stored for use by the physician when the patch is required after surgery.

Without further elaboration, the foregoing will so fully illustrate my invention that others may, by applying future knowledge, adopt the same for use under various conditions of service.

What is claimed as the invention is:

1. An eye patch for preventing opening of an eye, said patch comprising a compressible planar pad having a configuration which fits within the eye socket to contact the surface over a closed eye, said planar pad being flexible to conform to the outer surface of the lid of the eye, one surface of said pad having an adhesive layer over the entire area thereof, said adhesive layer being totally unobstructed such that the entire adhesive layer can be applied to directly contact with the outer surface of said eyelid and the eyelashes, said adhesive layer having a low to moderate adhesion such that said eye patch may be removed with minimal patient discomfort and with substantially no removal of eyelashes.

2. The patch of claim 1 wherein said patch includes at least one opening to permit application of fluids to the eye without removing said patch from the outer surface of said lid.

3. The patch of claim 2 wherein said opening is formed by removal of a portion of said pad so that the eyelid is visible therethrough.

4. The patch of claim 2 wherein a plurality of openings are provided and said openings form a plurality of strips which extend over and are secured to the eyelid to prevent opening of said eye until said patch is removed.

5. The patch of claim 1 wherein said pad comprises an open cell foam to permit air and fluids to be passed to the eye under said patch.

6. The patch of claim 1, 2, 4 or 5 wherein said pad has connected thereto a tab which extends laterally from a portion of said pad covering said eye, said tab having an adhesive layer on one surface.

7. The invention of claim 1 wherein a plurality of eye patches are provided in a strip of packaging comprising a top and bottom sheet having a sealable surface, said sheets being heat sealed together to provide a compartment for two of said eye patches, said packaging being heat sealed along the longitudinal edges of said sheets to form a strip of said packaging with pairs of eye patches being separated by transversely extending edges which with said longitudinally sealed edges form a sealed sterile package for each pair of patches, each of said transverse strips having means for facilitating the separation of a pair of eye patches from said strip of packaged eye patches.

8. The patch of claim 7 wherein said transverse edges are perforated along an axis thereof to facilitate ripping of each package of patches from said strip of packages.

* * * * *